(12) United States Patent
Salin-Nordstrom (10) Patent No.: US 6,897,061 B1
(45) Date of Patent: May 24, 2005

(54) TRANSDIFFERENTIATION OF GLIAL CELLS

(75) Inventor: Tuija Helina Salin-Nordstrom, Santa Monica, CA (US)

(73) Assignee: Spinal Cord Society, Fergus Falls, MN (US)

( * ) Notice: Subject to any disclaimer, the term of this patent is extended or adjusted under 35 U.S.C. 154(b) by 7 days.

(21) Appl. No.: 09/644,498

(22) Filed: Aug. 23, 2000

Related U.S. Application Data (60) Provisional application No. 60/212,240, filed on Jun. 16, 2000.

(51) Int. Cl.$^7$ .............................. C12N 5/02; C12N 5/08
(52) U.S. Cl. ....................... 435/325; 435/352; 435/353; 435/354; 435/366; 435/368; 435/377
(58) Field of Search .................................. 435/325, 352, 435/353, 354, 366, 368, 377, 363; 424/93.1

(56) References Cited

U.S. PATENT DOCUMENTS

| | | | |
|---|---|---|---|
| 4,444,760 A | 4/1984 | Thomas, Jr. | 424/177 |
| 5,082,670 A | 1/1992 | Gage et al. | 424/520 |
| 5,175,103 A | 12/1992 | Lee et al. | 435/172.3 |
| 5,411,883 A | 5/1995 | Boss et al. | 435/240.2 |
| 5,439,818 A | 8/1995 | Fiddes et al. | 435/240.2 |
| 5,514,566 A | 5/1996 | Fiddes et al. | 435/69.1 |
| 5,589,375 A | 12/1996 | Ullrich et al. | 435/240.2 |
| 5,589,376 A | 12/1996 | Anderson et al. | 435/240.2 |
| 5,618,531 A | 4/1997 | Cherksey | 424/93.7 |
| 5,654,183 A | 8/1997 | Anderson et al. | 435/172.3 |
| 5,672,499 A | 9/1997 | Anderson et al. | 435/240.4 |
| 5,750,103 A | 5/1998 | Cherksey | 424/93.21 |
| 5,750,376 A | 5/1998 | Weiss et al. | 435/69.52 |
| 5,753,505 A | 5/1998 | Luskin | 435/375 |
| 5,753,506 A * | 5/1998 | Johe | 435/377 |
| 5,762,926 A | 6/1998 | Gage et al. | 424/93.21 |
| 5,792,900 A | 8/1998 | Lee et al. | 800/2 |
| 5,849,553 A | 12/1998 | Anderson et al. | 435/172.3 |
| 5,851,832 A | 12/1998 | Weiss et al. | 435/368 |
| 5,928,947 A | 7/1999 | Anderson et al. | 435/455 |
| 5,958,767 A | 9/1999 | Snyder et al. | 435/368 |
| 5,968,829 A | 10/1999 | Carpenter | 435/467 |
| 5,980,885 A | 11/1999 | Weiss et al. | 424/93.21 |
| 5,981,165 A | 11/1999 | Weiss et al. | 435/4 |
| 6,001,654 A | 12/1999 | Anderson et al. | 435/377 |
| 6,033,906 A | 3/2000 | Anderson | 435/325 |
| 6,040,180 A * | 3/2000 | Johe | 435/377 |
| 6,060,048 A | 5/2000 | Cherksey | 424/93.1 |
| 6,071,691 A | 6/2000 | Hoekstra et al. | 435/4 |
| 6,071,889 A | 6/2000 | Weiss et al. | 514/44 |
| 6,087,168 A | 7/2000 | Levesque et al. | 435/345 |
| 6,103,530 A | 8/2000 | Carpenter | 435/405 |
| 6,184,200 B1 | 2/2001 | Hu | 514/12 |
| 6,361,996 B1 * | 3/2002 | Rao et al. | 435/353 |
| 6,497,872 B1 | 12/2002 | Weiss et al. | 424/93.1 |
| 2003/0032181 A1 * | 2/2003 | Weiss et al. | 435/368 |
| 2003/0059939 A1 * | 3/2003 | Page et al. | 435/366 |
| 2003/0109041 A1 * | 6/2003 | Rao et al. | 435/368 |

FOREIGN PATENT DOCUMENTS

| | | |
|---|---|---|
| WO | WO 93/01275 | 1/1993 |
| WO | WO 02/14479 | 2/2002 |

OTHER PUBLICATIONS

Gage et al. (1995) "Isolation, Characterization, and Use of Stem Cells from the CNS." Annu. Rev. Neurosci. 18: 159–192.*
Chanas–Sacre et al. (2000) "Radial Glia Phenotype: Origin, Regulation, and Transdifferentiation" Journal of Neuroscience Research 61: 357–363.*
Nolte, The Human Brain: An Introduction to Its Functional Anatomy, Mosby 4th Edition, pp. 23,31, 35, FIG. 1–26, and Table 1–3, 1999.*
Rao Multipotent and Restricted Precursors in the Central Nervous System, The Anotomical Record 257: 137–148, 1999.*
Kandel et al., Principles of Neural Science McGraw–Hill 4$^{th}$ Edition, pp. 67–81, 85–87, 2000.*
Rao et al. A Tripotential Glial Precursor Cell is Present in the Developing Spinal Cord, PNAS 95: 3996–4001, 1998.*
Lee et al. Gliogenesis in the Central Nervous System, Glia 30: 105–121, 2000.*
Laywell et al. (Dec. 5, 2000) "Identification of a multipotent astrocytic stem cell in the immature and adult mouse brain." PNAS 97(25): 13883–13888.*
Richards et al. (Sep. 15, 1992) "De novo generation of neuronal cells from the adult mouse brain." PNAS 89(18): 8591–8595.*
Sultana et al. (Apr. 2000) "Intermediate Filament Protein Synemin is Transiently Expressed in a Subset of Astrocytes During Development." Glia 30(2): 143–153.*
Gaul and Lübbert (1992) "Cortical astrocytes activated by basic fibroblast growth factor secrete molecules that stimulate differentiation of mesencephalic dopamingergic neurons." Proceedings of the Royal Society of London 249(1324): 57–63.*

(Continued)

Primary Examiner—Elizabeth C. Kemmerer
Assistant Examiner—Christopher James Nichols
(74) Attorney, Agent, or Firm—Patterson, Thuente, Skaar & Christensen, P.A.

(57) ABSTRACT

A process for generating multipotent cells from glial cells using in vitro techniques to dedifferentiate fetal or adult mammalian glial cells into multipotent cells. The multipotent cells may further be differentiated into particular types of nervous system cells, including neurons, astrocytes, and oligodendrocytes. A small sample of astrocytes is used to establish an in vitro culture of cells that is expanded and processed to yield multipotent cells that may be used directly or be differentiated to yield neurons and/or oligodendrocytes and/or astrocytes. The invention includes implanting the generated cells into patients. The invention includes a step of exposing the cells to a growth factor.

25 Claims, 3 Drawing Sheets

OTHER PUBLICATIONS

Sweetnam et al. (Jul. 1991) "Differential Effects of Acidic and Basic Fibroblast Growth Factors on Spinal Cord Cholinergic, GABAergic, and Glutamatergic Neurons." Journal of Neurochemistry 57(1): 237–249.*

Unsicker et al. (Oct. 1992) "Molecular control of neural plasticity by the multifunctional growth factor families of the FGFs an TFG–bs." Annals of Anatomy 174(5): 405–407.*

Morrison et al. (Sep. 1988) "Basic fibroblast growth factor and epidermal growth factor exert differential trophic effects on CNS neurons." Journal of Neuroscience Research 21(1): 71–79.*

Gray and Patel (Mar. 6, 1992) "Characterization of a neurotrophic factor produced by cultured astrocytes involved in the regulation of subcortical cholinergic neurons." Brain Research 574(1–2): 257–265.*

Seidman et al. (Apr. 4, 1997) "Isolation, cloning and characterization of a putative type–1 astrocyte cell line." Brain Research 753(1): 18–26.*

Petroski et al. (Sep. 1991) "Basic Fibroblast Growth Factor Regulates the Ability of Astrocytes to Support Hypothalamic Neuronal Survival in Vitro." Developmental Biology 147(1): 1–13.*

Walicke and Baird (May 1, 1988) "Neurotrophic effects of basic and acidic fibroblast growth factors are not mediated through gl cells." Developmental Brain Research 468(1): 71–79.*

C. Morshead et al., Postmitotic Death is the Fate of Constitutively Proliferating Cells in the Subependylmal Layer of the Adult Mouse Brain, *Journal of Neuroscience,* 12(1):249–256, 1992.

B. Reynolds et al., Generation of Neurons and Astrocytes from Isolated Cells of the Adult Mammalian Central Nervous System, *Science,* 255:1707–1710, 1992.

P. Lipton et al., Part One: Neurotrophic Factors—An Overview *Promega Notes Magazine,* 50:18 et seq., 1995.

K. Palm et al., Fetal and Adult Human CNS Stem Cells have Similar Molecular Characteristics and Developmental Potential, *Molecular Brain Research,* 78(1–2):192–195, 2000.

T. Newman et al., Isolation of Genes which Block Neuronal Differentiation of Teratocarcinoma PCC7 Cells, Experimental Cell Research, 217(2):363–367, 1995.

T. Neuman, Preclinical Trials on Parkinsonism, *Spinal Cord Society Newsletter,* 263:3–10, 2000.

T. Neuman, Cell Therapy of Human Spinal Cord Injury, *Spinal Cord Society Newsletter,* 259:6–9, 2000.

D. Stuart Ph.D., Annual Report of Research at UAB—SCS New Zealand Fellow, *Spinal Cord Society Newsletter,* 258: 9–10, 2000.

T. Neuman, Cell Therapy of Human Spinal Cord Injury, *Spinal Cord Society Newsletter,* 254:4–6, 2000.

T. Neuman et al., Cell Therapy II, *Spinal Cord Society Newsletter,* 247:3–5, 1999.

L. Studer, et al., Transplantation of Expanded Mesencephalic Precursors Leads to Recovery in Parkinsonian Rats, *Nature Neuroscience,* Aug. 1998, vol. 1, No. 4, pp. 290–295.

Survival of expanded Dopaminergic Precursors is Critical for Clinical Trials, *Nature Neuroscience,* Nov. 1998, vol. 1, No. 7, p. 537.

R. Barker et al., Functional Integration of Neural Grafts in Parkinson's Disease, *Nature Neuroscience,* Dec. 1999, vol. 2, No. 12, pp. 1047–1048.

P. Piccini et al., Dopamine Release from Nigral Transplants Visualized In Vivo in a Parkinson's Patient, *Nature Neuroscience,* Dec. 1999, vol. 2, No. 12, pp. 1137–1140.

P Cuevas, Role of fibroblast growth factors in neural trauma, Neurol Res 1997 19(3):254–256.

AO Wilkie et al., Functions of FGFs and their receptors, Curr Biol 1995 5(5):500–7.

Curr Opin Neurobiol 1994 4(1):78–86.

JK DOw et al., FGF2: its structure and property, paracrine function, Tumor angiogensis etc Urology 2000, 55(6):800–806.

A. Bikfalvi . . . DB Rikin, Biological; roles of FGF–2, Endocr Rev 1997, 18(1):26–45.

Gimenez–Gallego G, Cuevas P , Fibroblast growth factors, proteins with a broad spectrum of biological activities. Neurol Res Aug. 1994; 16(4):313–6.

MR Passos–Bueno et al., Clinical spectrum of FGF receptor mutations, Hum Mutat 1999 14(2):115–125.

Moffett J, Kratz E, Myers J, Stachowiak EK, Florkiewicz RZ, Stachowiak MK , Transcriptional regulation of fibroblast growth factor–2 expression in human astrocytes,: implications for cell plasticity; Mol Biol Cell Aug. 1998;9(8):2269–85.

Pincus DW, Keyoung HM, Harrison–Restelli C, Goodman RR, Fraser RA, Edgar M, Sakakibara S, Okano H, Nedergaard M, Goldman SA, Fibroblast growth factor–2/brain-derived neurotrophic factor–associated maturation of new neurons generated from adult human subependymal cells. Ann Neurol May 1998;43(5):576.

Palmer TD, Markakis EA, Willhoite AR, Safar F, Gage FH; Fibroblast growth factor–2 activates a latent neurogenic program in neural stem cells from diverse regions of the adult CNS. Neuroscie Oct. 1, 1999;19(19):8487–97.

Qian X, Davis AA, Goderie SK, Temple S ; FGF2 concentration regulates the generation of neurons and glia from multipotent cortical stem cells. Neuron Jan. 1997;18(1):81–93.

Chiang YH, Silani V, Zhou FC ; Morphological differentiation of astroglial progenitor cells from EGF–responsive neurospheres in response to fetal calf serum, basic fibroblast growth factor, and retinol. Cell Transplant Mar.–Apr. 1996;5(2):179–89.

Mujtaba T, Mayer–Proschel M, Rao MS ; A common neural progenitor for the CNS and PNS. Dev Biol Aug. 1, 1998;200(1):1–15.

Mackay–Sima A, Chuahb MI ; Neurotrophic factors in the primary olfactory pathway. Prog. Neurobiol Dec. 1, 2000;62(5):527–559.

Blanchard JM ; *Small GTPases, adhesion, cell cycle control and proliferation.* Pathol Biol (Paris) Apr. 2000;48(3):318–27.

Altschuler RA, Cho Y, Ylikoski J, Pirvola U, Magal E, Miller JM ; Rescue and regrowth of sensory nerves following deafferentation by neurotrophic factors. Ann N Y Acad Sci Nov. 28, 1999;884:305–11.

Lois and Alvarex–Buyalla, Science, 264:1145–1148, 1994.

Morshead et al., Neuron, 13:1071–1082, 1994.

Weiss et al., Trends in Neuroscience, 19:387–393, 1996a.

Weiss et al., Journal of Neuroscience, 16:7599–7609, 1996.

Doetsch F, Caille I, Lim DA, Garcia–Verdugo JM, Alvarez–Buylla A. zone astrocytes are neural stem cells in the adult mammalian brain.Cell. Jun. 11, 1999;97(6):703–16.

Svendsen et al., Experimental Neurology, 137:376–388, 1996.

Chalmers–Redman et al., Neuroscience, 76:1121–1128, 1997.
Carpenter et al., Experimental Neurology, 158:265–278, 1999.
Fricker et al., Journal of Neuroscience, 19:5990–6005, 1999.
Kudekov et al., Experimental Neurology, 156:333–334, 1999.
Vescovi et al., Experimental Neurology, 156, 71–83, 1999).
"*Survival and differentiation of adult neuronal progenitor cells* transplanted to the adult brain" by F.H. Gage et al., Proceedings of the National Academy of Science U.S.A. 92:11879–83 (1995).

"Self–repair in the brain" by A. Bjorklund and O. Lindvall, Nature 405:892–3, 895 (2000), which are hereby incorporated by reference.
I.J. Mason, "The ins and outs of FGFs", Cell, 1994 78:547–552.
A Baird, "FGFs: activities and significance of non–neurotrophin neurotrophic growth factors", Current Opinions in Neurobiology, 1994 4(1):78–86.
CJ Robinson, "Tailoring and targeting FGFs", Trends in Biotechnology 1991, 9(5):147–148.

* cited by examiner

Human          Rat

β-tubulin III

MAP2ab

CNPase

US 6,897,061 B1

TRANSDIFFERENTIATION OF GLIAL CELLS

REFERENCE TO RELATED APPLICATIONS

This application is related to U.S. Provisional Patent Application Ser. No. 60/212,240 entitled Transdifferentiation of Astrocytes into Neurons, filed Jun. 16, 2000, which is hereby incorporated by reference.

1.0 FIELD OF THE INVENTION

The invention relates to the in vitro transdifferentiation of mammalian cells from a glial cell type to neurons, oligodendrocytes, astrocytes, and associated type cells.

2.0 BACKGROUND OF THE INVENTION

Fetal neural progenitor, or stem cells are multipotent cells that are useful for various therapeutic applications involving their implantation into humans but significant moral, ethical, and technological issues make the use of these cells undesirable. Such problems include immunological rejection and potential contamination.

It has been reported that the entire ventricular neroaxis, including the spinal cords of adult mammals, contain stem cells (Morshead and Van der Kooy, Journal of Neuroscience, 12:249–256, 1992; Reynolds and Weiss, Science, 255:1707–1710, 1992; Lois and Alvarex-Buyalla, Science, 264:1145–1148, 1994; Morshead et al., Neuron, 13:1071–1082, 1994; Weiss et al., Trends in Neuroscience, 19:387–393, 1996a, Journal of Neuroscience, 16:7599–7609, 1996 b). These stem cells may proliferate and expand in some circumstances and are affected by growth factors such as epidermal growth factor (EGF), basic fibroblast growth factor (bFGF), leukemia inhibitor factor (LIF), and others; the stem cells may then differentiate into other cell types, including neurons, astrocytes, and oligodendrocytes (Reynolds and Weiss, 1992; Morshead et al., 1994; Weiss et al., 1996b). Recent data demonstrate that adult subventricular zone astrocytes or astrocyte progenitors can develop into stem cells in vivo (Doetsch, 1999).

An approach to isolating stem cells and differentiating them into other cell types has been reported. First, nervous system stem cells are isolated from human embryonic or adult brain; the technical and economic challenges of this technique make it difficult to use this process for producing cells for human implantation (Svendsen et al., Experimental Neurology, 137:376–388, 1996; Chalmers-Redman et al., Neuroscience, 76:1121–1128, 1997; Carpenter et al., Experimental Neurology, 158:265–278, 1999; Fricker et al., Journal of Neuroscience, 19:5990–6005, 1999; Kudekov et al., Experimental Neurology, 156:333–334, 1999; Vescovi et al., Experimental Neurology, 156, 71–83, 1999). These cells are transplanted into adult rodent brain, where they differentiate into neurons, glial cells, and associated cells, with no tumor formation (Vescovi et al., 1999).

A substantial body of literature describes therapies based on introducing cells into patients. These therapies include treatments of Alzheimer's, Parkinson's disease, and in vivo drug delivery. Examples of such therapies are described in "Survival and differentiation of adult neuronal progenitor cells transplanted to the adult brain" by F. H. Gage et al., Proceedings of the National Academy of Science U.S.A. 92:11879–83 (1995); "Site-specific migration and neuronal differentiation of human neural progenitor cells after transplantation in the adult rat brain" by R. A Fricker et al., Journal of Neuroscience, 19:5990–6005 (1999); and "Self-repair in the brain" by A. Bjorklund and 0. Lindvall, Nature 405:892–3, 895 (2000), which are hereby incorporated by reference.

3.0 SUMMARY OF THE INVENTION

The invention provides a practical approach for producing multipotent cells from non-fetal tissue. Astrocytes are directed to become multipotent cells. These cells are used directly or are differentiated to make particular cell types. The cells are taken from and transplanted back into the same person (autograft) or into another person (homologous graft). Alternatively, an animal source could be used for the cells which could be transplanted into humans (xenograft).

The invention provides techniques to transdifferentiate astrocytes into particular types of nervous system cells, including neurons, astrocytes, and oligodendrocytes. Only a small sample of astrocytes is needed to establish an in vitro culture of cells that may be expanded and processed to yield multipotent cells. The multipotent cells may be directly used or may be further processed to make neurons and/or oligodendrocytes and/or astrocytes. The method includes a step of exposing the cells to an added factor to make astrocytes dedifferentiate into multipotent cells. The added factor is a growth factor, including bFGF.

The invention includes implanting the cells into humans as part of therapies that call for implantation of fetal and/or stem cells. The invention provides methods for treating astrocytes with an added factor to produce multipotent cells that may be implanted. Alternatively, the invention may be practiced by producing multipotent cells and differentiating them in vitro to produce cells such as neurons that may be implanted.

The method of the invention includes: (1) establishing an in vitro culture of astrocytes; (2) optionally pretreating the cells in a medium with an added factor; (3) dissociating the cells and (4) treating the cells with an added factor. An alternative embodiment of the invention further includes (5) an in vitro differentiation step of growing the cells in a medium without the added factor so that the cells are differentiated into neurons, oligodendrocytes, and/or astrocytes.

A variety of growth factors are applicable as the added factor but neurotrophins are especially useful, including members of the Fibroblast Growth Factor (FGF) family. bFGF is an especially useful member of the FGF family. Experiments with bFGF indicate that other members of the FGF family as well as functionally related growth factors may be used in the invention. bFGF is a well-documented mitogen for many different cell types and other members of the FGF family display overlapping functions. In addition, other growth factors that have been shown to be mitogens for stem cells are applicable. In general, cells that respond to at least one of the growth factors described above are cells that express a palette of FGF receptors on their surfaces. And various multipotent cells isolated from the mammalian nervous system have been shown to express at least FGF-receptor-1, FGF-receptor-2 and FGF-receptor-3.

A substantial body of literature describes the Neurotrophin and FGF families, including the following references which are hereby incorporated by reference: Cuevas, "Role of fibroblast growth factors in neural trauma", Neurology Research, 1997 19(3):254–256; A. O. Wilkie et al., "Functions of FGFs and their receptors", Current Biology, 1995 5(5):500–7; I. J. Mason, "The ins and outs of FGFs", Cell, 1994 78:547–552; A Baird, "FGFs: activities and significance of non-neurotrophin neurotrophic growth factors", Current Opinions in Neurobiology, 1994 4(1):78–86; C J Robinson, "Tailoring and targeting FGFs", Trends in Biotechnology 1991, 9(5):147–148; JK Dow et al., "FGF2: its structure and property, paracrine function, tumor angiogensis . . . " Urology, 2000, 55(6):800–806; A. Bikfalvi et al., "Biological roles of FGF-2", Endocrine Reviews, 1997, 18(1):2645; Gimenez-Gallego G, Cuevas P, "Fibroblast growth factors, proteins with a broad spectrum of biological activities", Neurological Research 1994, 16:313–6; M R Passos-Bueno et al., "Clinical spectrum of FGF receptor mutations", Human Mutatation 1999, 14(2):115–125; Moffett J, et al., "Transcriptional regulation of fibroblast growth factor-2 expression in human astrocytes: implications for cell plasticity", Molecular Biology of the Cell, 1998, 9:2269–85; Pincus D W et al., "Fibroblast growth factor-2/ brain-derived neurotrophic factor-associated maturation of new neurons generated from adult human subependymal cells", Annals of Neurology, 1998, 43:576 et seq.; Palmer TD et al., "Fibroblast growth factor-2 activates a latent neurogenic program in neural stem cells from diverse regions of the adult CNS", Neuroscience, 1999 19:8487–97; Qian X, et al., "FGF2 concentration regulates the generation of neurons and glia from multipotent cortical stem cells", Neuron, 1997, 18:81–93; Chiang Y H, Silani V, Zhou F C; "Morphological differentiation of astroglial progenitor cells from EGF-responsive neurospheres in response to fetal calf serum, basic fibroblast growth factor, and retinol", Cell Transplantation, 1996, March–April; 5:179–89; Mujtaba T, Mayer-Proschel M, Rao M S "A common neural progenitor for the CNS and PNS", Developmental Biology, 1998, 200(1):1–15; Mackay-Sima A, Chuahb M I "Neurotrophic factors in the primary olfactory pathway", Progress in Neurobiology, 2000, 62:527–559; Blanchard J M "Small GTPases, adhesion, cell cycle control and proliferation", Pathologie Biologie (Paris), 2000, 48(3):318–27; Altschuler R A, Cho Y, Ylikoski J, Pirvola U, Magal E, Miller J M "Rescue and regrowth of sensory nerves following deafferentation by neurotrophic factors", Annals of the New York Academy of Science, 1999, 884:305–11.

The invention further includes methods for identifying biological agents that have transdifferentiation activity. The prior art does not have protocols for detecting agents that cause transdifferentiation. The protocol for identifying such agents includes culturing astrocytes, disassociating them, plating them into test wells, adding a test growth factor, growing the cells in the presence of the growth factor, determining the cells types in the test wells, and running appropriate controls. The test wells are any suitable means for culturing cells, including petri dishes, multiwell plates, culture flasks, etc. A preferred positive control is a test well with bFGF.

The invention may be used for a variety of autologous, homologous, and xenotransplantation applications, including replacement of lost and defective cells and delivery of therapeutic products. It may be used, for instance, in intracerebral implantation treatments. The invention may be used for therapeutic applications including Alzheimer's, Parkinson's disease, and recovery from stroke or accidental damage to the brain or spinal cord. The invention may be used for drug design and drug testing. The invention includes methods for screening growth factors that accomplish transdifferentiation of astrocytes.

The invention provides a renewable source of multipotent mammalian cells that will be invaluable for clinical studies and treatments of neural diseases, including neurotrauma and/or neurodegenerative diseases. The invention provides for the transdifferentiation of astrocytes into multipotent cells and for use of the multipotent cells directly or after they have been transdifferentiated into neurons, astrocytes, and/or oligodendrocytes. The cells may be derived from adult tissue and eliminate the need for other types of cells such as human fetal cells. The multipotent cells are derived from astrocytes, which are easily, predictably, and economically obtained compared to current methods of directly isolating stem cells or using fetal tissue. The multipotent cells of the invention are readily obtained in the abundant amounts required for implantation, and are kept on hand locally or may be stored at a central location for rapid shipping to medical facilities.

5.0 DETAILED DESCRIPTION OF THE PREFERRED EMBODIMENTS

A method of the present invention produces multipotent cells from astrocytes. The astrocytes may pass through a stage of transdifferentiation to a multipotent cell type that may in turn be differentiated into a neuron, oligodendrocyte, or an astrocyte. Astrocytes are cultured in vitro, optionally pretreated with a growth factor, undergo a dissociation step, and are then cultured in the presence of an added factor like bFGF, a process that causes the cells to become multipotent. The multipotent cells may be used in their multipotent state or differentiated into neurons and/or oligodendrocytes and/or astrocytes by culturing the cells without the added factor. The culture conditions are manipulated to change the yield of cells and particular cell types.

Cells differentiate from multipotent cells to more differentiated specialized cell types. A "multipotent" cell is a cell that may differentiate into more than one cell type. Thus an astrocyte that dedifferentiates or transdifferentiates into a multipotent cell could then differentiate into an astrocyte or some other cell type. "Transdifferentiation" refers to a process whereby a cell is changed from one cell type to another cell type; transdifferentiation may or may not involve dedifferentiation or an intermediate stage of being multipotent. "Cultured" and "grown" are interchangeably used when referring to the in vitro cultivation of cells and include the meaning of expansion or maintenance of a cell population. DMEM/F12 medium refers to a commonly available cell culture medium that is a mixture of "Dulbebco's modified Eagle Medium" and "F-12" medium.

The term an "added factor" is a growth factor that a user places in contact with cells. Such contact is accomplished by many alternative means, including adding the factor to the medium, co-culturing the cells with other cells that produce the factor, adding precursors of the factor that are subsequently converted in vitro to the factor, immobilizing the factor on the culture substrate in an active form, and inducing cells in the culture to express the factor. An added factor is at least one factor and may be a combination of factors.

A "growth factor" refers to the class of biologically active compounds known as "growth factors". Similar growth factors are grouped into subclasses called families. A family of growth factors is the neurotrophins. The neurotrophin family includes the smaller groups known as the fibroblast growth factor (FGF) family and the neuropetic cytokine family (Peter Lipton and Ronald Kalil, "Part One: Neurotrophic Factors—An Overview" Promega Notes Magazine, Number 50, 1995, page 18 et seq.).

The term "growth factor" includes not only growth factors but also the equivalents that are commonly known to those skilled in these arts; such equivalents are included in the invention. Many techniques for making such equivalents are well known and obvious to the average artisan. Such equivalents are numerous and include but are not limited to: fragments of the growth factor that mimic the activity of all or part of the growth factor; growth factor agonists; antibodies that activate a receptor targeted by the growth factor; agents that react with the cell receptors that the growth factor reacts with; biologically active peptides derived from the growth factor, fragments or peptides with amino acid substitutions that do not eliminate biological activity; immobilization or attachment or co-expression of the growth factor and/or fragment and/or peptide to a surface or another molecule or a biological agent; precursors to the growth factor; variants of the growth factor; synthetic agents that perform the same function as the growth factor; natural agents, for instance cytokines, that imitate growth factor activities; transfection with genetic sequences to induce expression of the growth factor; co-culture with cells that produce the growth factor; agents that bypass the cell surface receptor and directly activate second messenger pathways; mixtures of "unknown" biological agents that are likely to contain the growth factor; and compositions that contain the growth factors in a biologically active component. Analogously, removal of an added factor that is a growth factor may be accomplished in many ways, including: changing to culture medium that has no added factor, suppressing the added factor with inactivating antibodies, and inducing expression of a counter-acting factor or agent.

As a result of reading this disclosure, an ordinary person skilled in these arts will understand how to derive a variety of particular cell types from astrocytes and many additional applications and implications of this work. This disclosure is not intended to limit the scope of the invention described herein as many derivations and variations of the embodiments are within the scope and spirit of the invention. The embodiments and experiments that are disclosed are only examples of the invention. Publications referred to herein are hereby incorporated by reference.

Further, after reading this disclosure, many variations on the concentrations and variety of components used in the methods and media will be understood as being useful. For instance, it is commonly known that the effects of a biologically active compound on a living system are often a product of time and concentration. So use of a lower concentration of a growth factor for a longer time will often have an effect similar to use of a higher concentration of the compound for a shorter time. On the other hand, some growth factors such as bFGF support survival at low concentrations but promote proliferation at higher concentrations. A person skilled in these arts, however, after reading this disclosure, may readily determine the useful or optimal concentrations and combinations of media components using standard cell culture techniques.

LIFE TECHNOLOGIES, INC. manufactures media and reagents under its GIBCO BRL trademark. Detailed compositions and properties of the GIBCO products used in the methods described herein are reported in the current GIBCO catalog (for the year 2000); in general, these products have concentrations, purities, and activities that are within the range typically used in the life sciences industry. Also, the manual written by Ian Freshney (Culture of Animal Cells—A Manual of Basic Technique, Alan R. Liss, NY, 1987) describes typical media compositions, including DMEM/F 12 and other typical serum-free media compositions for culture of a wide range of cells. These publications are hereby expressly incorporated by reference.

dbcAMP is dibutyrl cyclic adenosine monophosphate. BDNF is brain derived neurotrophic factor. GDNF is glial derived neurotrophic factor. RA is retinoic acid, preferably all-trans. AA is ascorbic acid. B27 is GIBCO B27 supplement. NEUROBASAL is a GIBCO medium. The neurotrophin family includes nerve growth factor (NGF), brain derived neurotrophic factor (BDNF), neurotrophin-3 (NT-3) and neurotrophin-4/5 (NT-4/5). CNTF is Ciliary Neurotrophic Factor. Other abbreviations are: retinoic acid (RA); ascorbic acid (AA); fetal calf serum (FCS); glial fibrillary acidic protein (GFAP); and 2',3'-cyclic nucleotide 3'-phosphodiesterase (CNPase); milliliter (ml); nanogram (ng).

5.1 Establishment of an In Vitro Culture of Glial Cells

Glial cells may be isolated from different parts of the fetal or adult mammal central or peripheral nervous system. There are numerous protocols known to those skilled in the art of cell culture (for instance, see R. Freshney, 1987, Culture of Animal Cells: A Manual of Basic Technique, Alan R Liss Inc., New York). The cells may also be obtained from sources of transformed cells or commercial sources. The cells may be populations of only one cell type or may have more than one cell type. Glial cells refers to a class of cell types that includes astrocytes. The invention may be practiced with astrocytes or other glial cells.

Culturing of primary cells involves isolating nervous tissue from a sample of fetal or adult tissue, rinsing in physiologically balanced saline such as phosphate buffer solution (PBS), and cutting the tissue into small pieces, typically about 2×2 millimeters. The tissue fragments are treated with a dissociation solution such as an enzyme-free solution (e.g., VERSENE; GIBCO) and/or an enzymatic solution such as a collagenase or trypsin solution. The cells are exposed to a trypsin inhibitor, for instance soybean trypsin inhibitor or other commonly available inhibitors. The cells are mechanically dissociated, for instance by trituration using a plastic Pasteur pipette to obtain a suspension with single cells. The cells are centrifuged into a pellet, washed and plated onto plastic tissue culture flasks at about 2000–4000 cells per $cm^2$. Glial cells are cultured in DMEM/F 12 medium (GIBCO) supplemented with 5%–15% fetal calf serum (GIBCO) at 37 degrees C. in a 5% $CO_2$ atmosphere or in other commercially available serum-free medium formulations. The medium is changed approximately twice per week and the cells are passaged at 1:2 ratio after reaching confluency. These procedures may be used to establish cultures of cells, including monolayers of astrocytes.

5.2 Pretreatment Step of Culturing Cells

A pretreatment step is optionally performed by growing a group of cells with a growth factor prior to dissociation the cells. bFGF is an effective factor for pretreatment that increases the number of neurons that develop. This step is preferable but optional and the pretreatment growth factor may be the same or different from the treatment growth factor. The bFGF is preferably administered with heparin or the like. A suitable protocol is to wash a monolayer of astrocytes in medium; culture in DMEM/F-12 plus SUPPLEMENT B27 (GIBCO), 20-ng per ml bFGF, and heparin (1 microgram per milliliter, SIGMA); and grow the cells for about one to two days prior to dissociating them.

5.3 Dissociation of Cultured Cells

Cultured cells that have preferably been pretreated are preferably dissociated and plated onto a suitable substrate with a ratio of better than 1:5. Dissociation is the process of breaking cell-to-cell and cell-to-surface associations. Trypsin and/or mechanical action is used to dissociate the cells. A suitable protocol is to wash cultured cells in PBS, incubate in 0.25% trypsin for two minutes at 37 degrees C., add trypsin inhibitor solution, pellet the cells by centrifugation, wash the cells once in PBS, and plate onto tissue culture plastic.

5.4 Treatment Step for Culturing Cells

Cells that have preferably been dissociated are plated onto a substrate such as tissue culture plastic. Cells are preferably plated at a high density of more than 7000 cells per $cm^2$ and treated by growing them in chemically defined culture medium (DMEM/F12) containing SUPPLEMENT B27, an effective dose of an added growth factor. Half of this media is replaced every three days. In the range of approximately 10 to 14 days the cells form clusters that are collected and mechanically dissociated once per week. bFGF is an example of an effective added factor.

This process produces multipotent cells that are used directly or may be maintained in cultures for future use. Alternatively, the multipotent cells are further treated with an in vitro differentiation step that produces neurons, astrocytes, and/or oligodendrocytes.

5.5 In Vitro Differentiation Step of Culturing Cells

After the treatment step, the cells undergo an in vitro differentiation step that deprives the cells of the added factor used in the treatment steps. The in vitro differentiation step helps the cells transdifferentiate into various cell types including astrocytes, oligodendrocytes, and neurons. The cells may be cultured in various differentiation media that provide factors for cell survival. Suitable media includes a chemically defined medium such as DMEM/F12 supplemented with 1 $\mu$M RA, 1 mM dbcAMP and 30 ng per ml BDNF (Medium I); 30 ng per ml BDNF (Medium II); or 20 ng per ml GDNF, 10 ng per ml FGF-8, and 100 $\mu$M AA (Medium III). A medium supplemented with NEUROBASAL medium is also suitable (GIBCO). The cells are cultured on a substrate coated with laminin, poly-L-lysine, polyomithine, a suitable extracellular matrix factor, or the like.

The type of cells produced by this method is steered by a number of variables, especially by the choice of the growth factor in the pre-treatment step, the growth factor in the treatment step, the medium in the in vitro differentiation step, and the duration of the steps. NEUROBASAL medium is preferable for developing neurons and Media 1, II, and III are also effective. Medium III is preferable for developing oligodendrocytes and Medium I is preferable for minimizing the number of oligodendrocytes.

Cells may respond differently to a growth factor in the treatment and/or pretreatment and/or in vitro differentiation step because they are in different stages of transdifferentiation. Therefore a first protocol uses a first growth factor in the treatment step and remove it in the in vitro differentiation step but an alternative protocol uses the first growth factor as an additive in the in vitro differentiation step while using a different growth factor in the treatment step.

Other steps may be desirable after the in vitro differentiation step and are contemplated in the invention. For instance, after a desirable number of neurons have been established in a culture, a growth factor that enhances neuronal survival may be added. bFGF is a growth factor that has a survival (trophic) effect. Other factors include the neurotrophin family of growth factors.

5.6 Use of Markers to Identify Cells

The types of cells in the culture are identified by a variety of methods including means of visualizing cell markers, for example by using labeled antibodies that recognize the markers on the cells. In brief, cell cultures are fixed in 4% paraformaldehyde, washed in PBS, permeabilized with 0.1% TRITON X-100, and incubated with 4% serum in PBS with 0.1% TRITON X-100. Cells are then incubated with primary antibodies in blocking solution for at least 3 hours at room temperature.

Suitable immunocytochemical markers on the cells are MAP2ab and Beta-tubulin III for neurons; GFAP protein for astrocytes; and 04 and CNPase molecules for oligodendrocytes.

5.7 Screening of Growth Factors and Equivalent Agents

This protocol sets forth a method to screen growth factors for transdifferentiation. In one method, astrocytes are cultured as a monolayer in the presence of DMEM/F 12 and 10% FCS and dissociated according to the standard method described above at 5.3, preferably using trypsin. The cells are replated at 7000 cells per $cm^2$ onto standard cell culture plastic 6-well plates, one plate per growth factor to be examined. Cells are cultured in duplicate wells for 14–21 days in DMEM/F-12 supplemented with B27 supplement and in the presence of three different concentrations (preferably 0.5, 20.0 and 100.0 ng per ml) of the growth factor. As a positive control, cells are grown in another well of a 6-well plate in DMEM/F-12/B27 and in the presence of 20-ng per ml bFGF and as a negative control cells are grown in DMEM/F-12/B27. Fresh medium containing the growth factor is added every second or third day. Once a week, the cells are collected and mechanically dissociated. After 14–21 days cells are mechanically dissociated and replated on laminin-coated cell culture plastic for differentiation. The cells are grown for 7–14 days in DMEM/F-12 or NEUROBASAL cell culture medium both supplemented with B27 and in the absence of the growth factor to be examined.

Cells are examined using antibody markers as described at 5.6. For each antibody, cells are plated in duplicates. Beta-tubulin III and MAP2ab antibodies are used to detect neurons. GFAP is used to detect astrocytes. CNPase is used to detect oligodendrocytes.

This protocol is described in terms of growth factor screening with mammalian astrocytes but is adaptable to other circumstances as suggested by this Application. This protocol enables artisans of ordinary skill to screen agents for transdifferentiation. This protocol provides considerable guidance to artisans wishing to practice screening of agents for transdifferentiation of astrocytes.

6.0 EXAMPLE 1

Analysis of Astrocytes Treated with bFGF

A series of experiments are grouped together in this example to show conditions for the culture of cells and treatments for transdifferentiation.

6.1 In Vitro Culture of Astrocytes

6.1.1 In Vitro Culture of Astrocytes from Human Neural Progenitor Cell Derived Astrocytes Astrocytes derived from human neural stem cells were grown on plastic tissue culture flasks in the presence of 10% FCS in DMEM/F-12 culture medium. The media was changed twice per week. After confluency, the cells were trypsinized (0.25% trypsin for 2 minutes at 37 degrees C.), treated with trypsin neutralization solution (CALBIOCHEM) and the cells were pelleted, resuspended and plated at a ratio of 1:3. In general, it was important to passage the cells at no more than 1:5 ratio; further, at a 1:2 ratio confluency was typically achieved in 7–10 days.

6.1.2 In Vitro Culture of Mammalian Astrocytes from Mammalian Nervous Tissue

Nervous tissue was isolated from a sample of adult tissue, rinsed in phosphate buffer solution (PBS; obtained from GIBCO), and cut into small pieces, about 2×2 millimeters. The tissue fragments were incubated in trypsin solution (0.25% trypsin solution in VERSENE Solution, GIBCO) for 10 minutes at 37 degrees C., inhibited with trypsin with trypsin inhibitor solution (GIBCO), and mechanically dissociated into a single cell suspension using a plastic Pasture Pipette. The suspension was centrifuged at 700 g for 3 minutes, the resulting cell pellet was washed with PBS and cells were plated onto plastic tissue culture flasks (FALCON) at 2000–4000 cells per $cm^2$. Cells were cultured in DMEM/F12 medium (GIBCO) supplemented with 5%–15% fetal calf serum (GIBCO) at 37 degrees C. in a 5% $CO_2$ atmosphere. The medium was changed twice per week and after reaching confluency the cells were passaged at 1:2 ratio.

6.1.3 Morphology of Cells

The cultured cells consisted mainly of large irregular or flat cells (type I astrocytes), a smaller population of stellat-like cells, morphologically type-2 astrocytes, and a smaller number of oligodendrocytes. The proportion of cells with an astrocyte type I morphology became greater as time passed.

6.1.4 Expression of Cell Marker Proteins in Cultures

Immunocytochemistry was performed to identify markers on the cells to verify the identity of the various cell types. Cell cultures were fixed twenty minutes at room temperature with 4% paraformaldehyde in PBS, and washed thrice in PBS. The fixed cells were permeabilized using 0.1% TRITON X-100 and nonspecific antibody binding was blocked by incubation with 4% donkey serum in PBS with 0.1% TRITON X-100 for at least 1 hour at room temperature. Blocking was followed by incubation with primary antibodies in the same blocking solution for at least 3 hours at room temperature.

The immunocytochemical markers for the cells were: MAP2ab and Beta-tubulin III (CHEMICON) for neurons; GFAP protein (CHEMICON) for astrocytes; and O4 (BOEHRINGER) and CNPase (CHEMICON) molecules indicated oligodendrocytes.

The cells in the cultures expressed no Beta-tubulin III or MAP2ab, indicating that there were no neuronal cells. More than 99% of the cells expressed GFAP, indicating that they were astrocytes. A very low number of cells co-expressed O4 and CNPase, indicating that a small number of cells were oligodendrocytes.

6.2 Pretreatment and Treatment of Cultured Cells with bFGF

Figure 1:
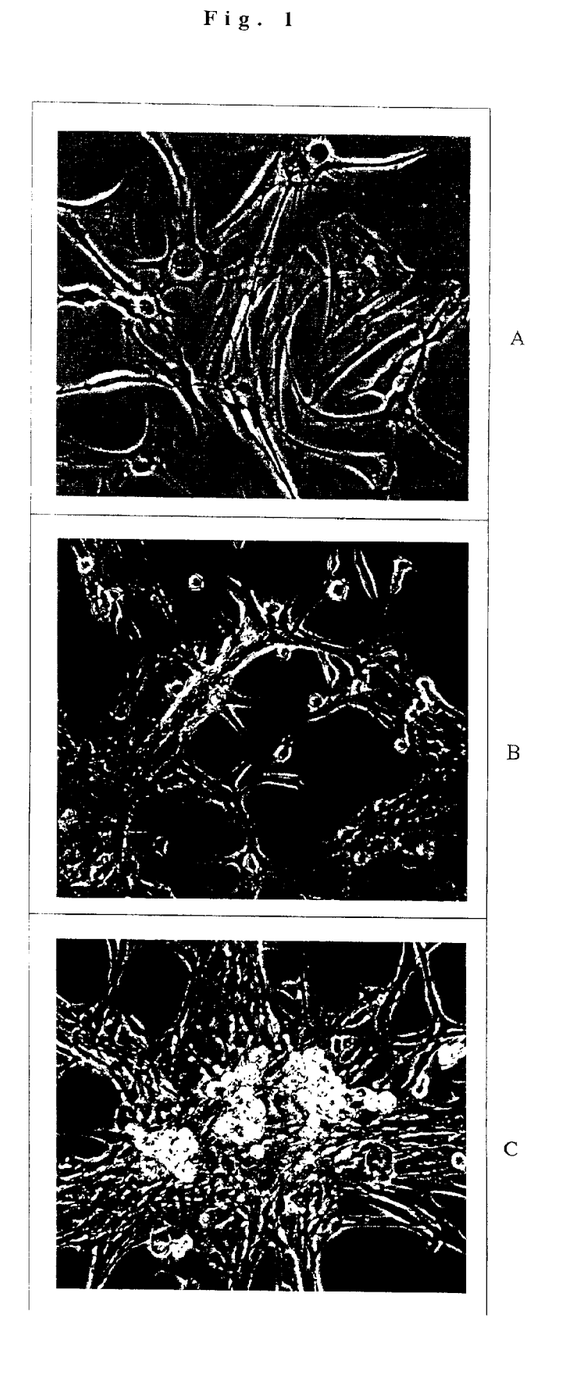
FIG. 1 is a photomicrograph of untreated astrocytes (A) and astrocytes pretreated with bFGF (B and C).

The monolayer of cells was pretreated with bFGF by washing once with DMEM/F-12 and culturing in chemically defined culture media (DMEM/F-12; GIBCO) containing SUPPLEMENT B27 (GIBCO), 20 ng per ml bFGF, and 1 microgram per ml heparin (SIGMA). Cells were grown approximately 1–2 days. The cultured cells initially had a flattened morphology (FIG. 1A) but after addition of the bFGF-containing medium had a more elongated morphology resembling reactive astrocytes (FIGS. 1B and 1C). The homogeneous monolayer was changed into bundles of cells and on a few occasions formed clusters.

Figure 2:
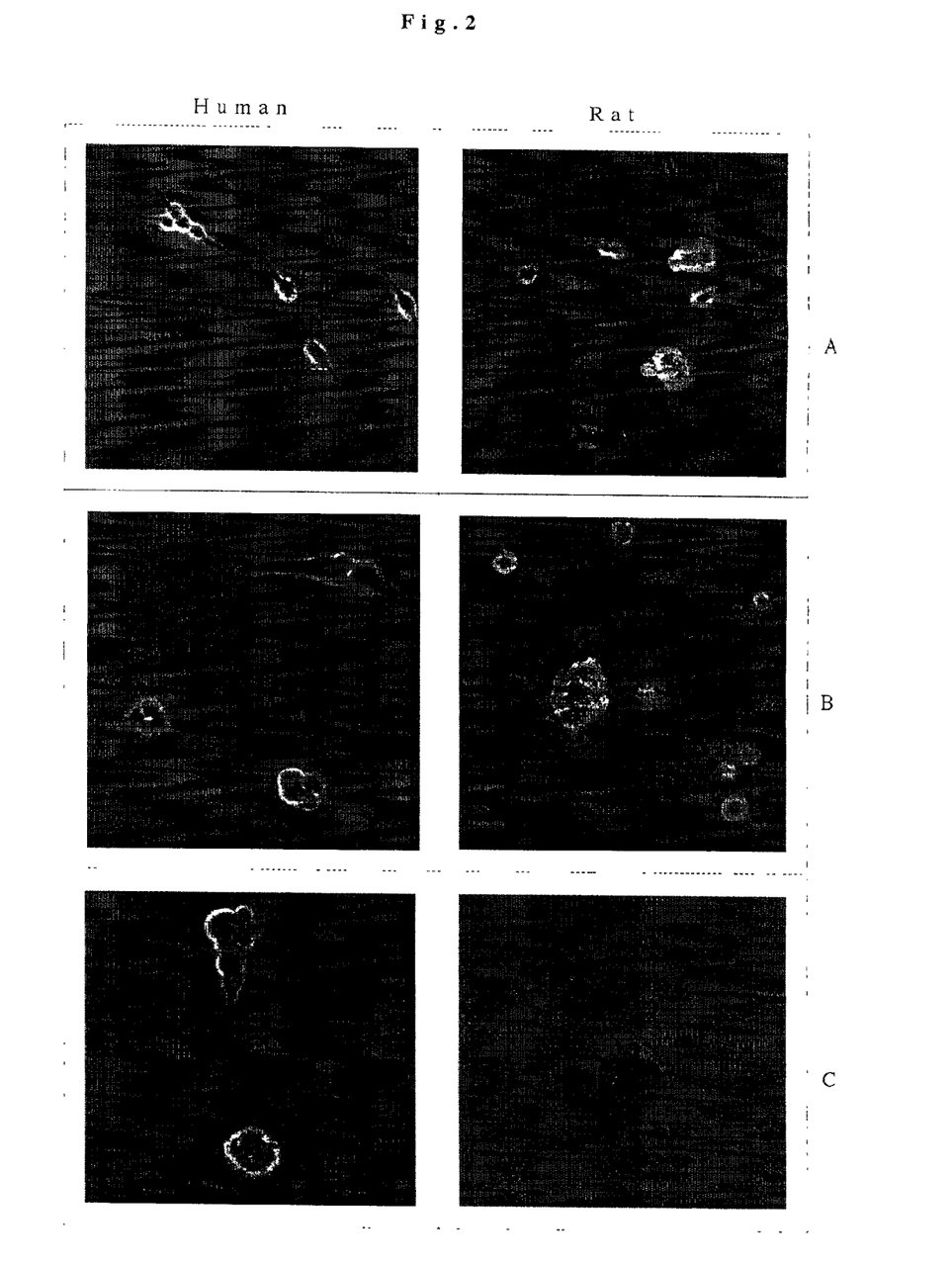
FIG. 2 is a photomicrograph of human and rat astrocytes treated with bFGF for 3 (A), 5 (B), and 7 (C) days.

The cells were dissociated by washing once in PBS and incubating with trypsin solution (0.25% in VERSENE; GIBCO) for 2 minutes at 37 degrees C. Trypsin inhibitor solution (GIBCO) was added and the cells were centrifuged and pelleted, washed once in PBS, and plated. The cells grew as aggregates, which is a morphology different than seen with bFGF pretreatment only (FIGS. 2A, 2B, 2C).

7.0 EXAMPLE 2

Treatment with bFGF without a Dissociation Step

The cells were treated as described in Example 1 except as described below, most notably in the omission of the trypsinization step. In brief, monolayers of astrocytes were washed once in DMEM/F-12 and defined medium containing DMEM/F-12 and SUPPLEMENT B27 (GIBCO), 20-ng per ml bFGF (PEPROTECH), and 1 microgram per ml heparin (SIGMA) was added for 2 and 5 days. The cells were then grown in Medium I for 7 days.

Immunochemistry revealed that there were no MAP2ab or Beta-tubulin III positive cells dissociation enhances the production of multipotent cells because cells that underwent the same treatment plus a dissociation step were made multipotent and then differentiated into neurons.

8.0 EXAMPLE 3

Pretreatment and Treatment of Cells with bFGF

These experiments were performed as described in Example 1 except for the differences described herein; these results are the results of multiple experiments. Cultured astrocytes were dissociated and plated on tissue culture plastic. The cells were cultured with 20 ng per ml bFGF plus heparin for three to six weeks. The cells were then placed in Medium I, Medium II, or Medium III for 7 and 14 days on laminin-coated substrates.

Figure 3:
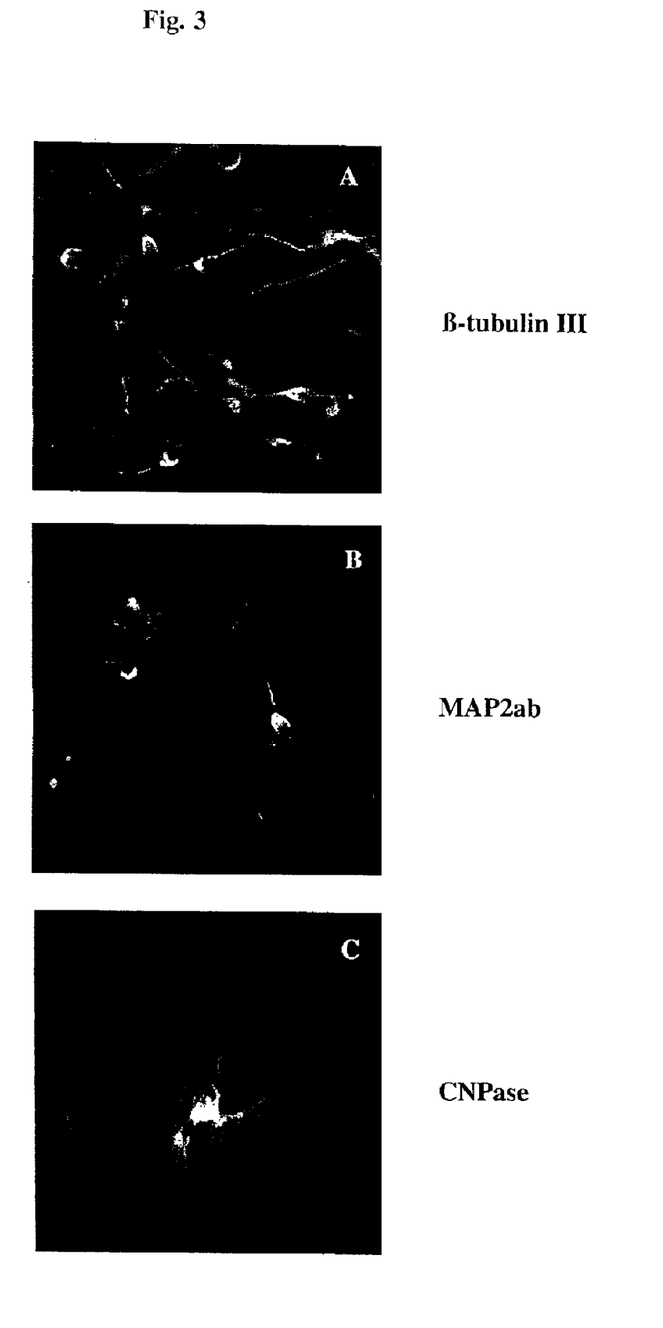
FIG. 3 is a photomicrograph of bFGF-treated cells that have been differentiated in Medium III, neurons positive for MAP2ab and Beta-tubulin III (A and B), oligodendrocytes positive for CNPasc (C) and astrocytes (not shown).

After 7 days in Medium I, II, or III, 60%–80% of the cells were GFAP positive astrocytes. Up to 30% of the cells were Beta-tubulin III positive, GFAP negative neurons (FIG. 3A) and 5–10% of the cells were MAP2ab positive. In Media II and III, 0.5%–2.0% cells were positive for the oligodendrocyte markers CNPase and O4. Cells in Medium II marked for CNPase and O4 were more strongly positive for these markers than cells in the other media. In Medium I oligodendrocytes were mainly absent. The MAP2ab and/or Beta-tubulin III positive neurons were not marked by the GFAP astrocyte marker and were morphologically distinct from the larger GFAP positive astrocytes and the few O4 and/or CNPase positive glial cells. Other experiments have shown that the percentage of neurons was as much as 30% if the plating density was high.

After 14 days in Medium I, II, or III, the amount of MAP2ab positive neurons was as much as 30% in high density cultures but 5% or less in low density cultures. High-density cultures had 5,000–10,000 cells per $cm^2$ but low-density cultures had less than approximately 1000 cells per $cm^2$. The MAP2ab positive neurons (FIG. 3B) were affected by differentiation factors and exhibited longer and more developed neurites and cell bodies in the presence of either Medium II or Medium III. CNPase positive oligodendrocytes (FIG. 3C) were the most numerous (1%–5%) in the Medium III cultures.

A parallel series of cultures of astrocytes were grown without exposure to bFGF and then in the presence of medium supplemented with serum instead of Medium I, II, or III. These cultures did not contain neurons as evidenced by observations that there were no MAP2ab-positive cells nor GFAP negative and Beta-tubulin III positive cells at any time point.

A control culture was performed in which astrocytes were grown without exposure to bFGF, were trypsinized, and then grown on laminin in Medium I or II or III. These cells were found to be more than 99% GFAP-positive astrocytes and no beta-tubulin III and/or MAP2ab-positive neurons were observed.

9.0 EXAMPLE 4

Treatment with bFGF

Cultures were performed as described in Experiment 1 except for the differences described herein. Astrocytes from human neural stem cells as per section 6.1.1 were exposed to chemically defined culture medium (DMEM/F12; GIBCO) containing SUPPLEMENT B27 (GIBCO), 20 ng per ml bFGF, and 1 microgram per ml heparin (SIGMA) for 1, 3, 6, 9, and 21 days. Cells were trypsinized and plated at 7000 cells per $cm^2$ onto plastic tissue culture plates (FALCON) and cultured in Medium II for 7 days. Cells that were Beta-tubulin III positive and GFAP negative were scored as neurons (See Table 1).

TABLE I

Time required for induction of neurites from astrocytes by bFGF treatment

| Time, days | neurons, % of cells |
| --- | --- |
| no bFGF treatment | 0 |
| 1 | <1 |
| 3 | 2 |
| 6 | 3 |
| 9 | 18 |
| 21 | 30 |

It is claimed:

1. An in vitro method to produce a population that includes neurons and/or oligodendrocytes, the method comprising:
    (a) obtaining and/or isolating a mammalian neural stem cell;
    (b) culturing said neural stem cell to produce an in vitro cell culture that includes astrocytes;
    (c) dissociating and plating the in vitro cell culture; and
    (d) maintaining the in vitro cell culture in medium essentially free of serum comprising bFGF for at least one day,
to produce a population of cells that include neurons and/or oligodendrocytes.

2. The method of claim 1, further comprising, before step (b), maintaining the in vitro cell culture in the presence of bFGF.

3. The method of claim 1, wherein step (c) maintaining the in vitro cell culture in medium comprising bFGF, is performed for at least 10 days.

4. The method of claim 1, wherein step (c) maintaining the in vitro cell culture in medium comprising bFGF for at least one day further comprises mechanically disrupting cell clusters.

5. The method of claim 1, further comprising, after step (c), maintaining the in vitro cell culture in a medium in the absence of bFGF.

6. The method of claim 5 wherein the medium comprises DMEM.

7. The method of claim 5 wherein the medium comprises F12.

8. The method of claim 5 wherein the medium comprises FGF-8.

9. The method of claim 5 wherein the medium comprises a member of the group consisting of retinoic acid, dbcAMP, BDNF, and GDNF.

10. The method of claim 1, wherein the cells are plated onto a substrate that comprises a member of the group consisting of poly L-lysine, polyornithine, and extracellular matrix.

11. The method of claim 1, wherein the concentration of the bFGF is in the range of 0.05 to 1000 ng per ml.

12. The method of claim 1, wherein heparin is present with the bFGF.

13. An in vitro method to screen a compound for trans-differentiation activity, the method comprising:
    (a) obtaining and/or isolating a mammalian neural stem cell;
    (b) culturing said neural stem cell to produce an in vitro cell culture that includes astrocytes;
    (c) dissociating and plating the in vitro cell culture; and
    (d) maintaining the in vitro cell culture in medium essentially free of serum comprising a compound for at least one day,
and performing, as a control, steps comprising:
    (a) obtaining and/or isolating a mammalian neural stem cell;
    (b) culturing said neural stem cell to produce an in vitro cell culture that includes astrocytes;
    (c) dissociating and plating the in vitro cell culture; and
    (d) maintaining the in vitro cell culture in medium essentially free of serum comprising bFGF for at least one day,
to produce a population of cells that include neurons and/or oligodendrocytes.

14. The method of claim 13, further comprising, before step (b), maintaining the in vitro cell culture in the presence of bFGF.

15. The method of claim 13, wherein step (c) maintaining the in vitro cell culture in medium comprising bFGF, is performed for at least 10 days.

16. The method of claim 13, wherein step (c) maintaining the in vitro cell culture in medium comprising bFGF for at least one day further comprises mechanically disrupting cell clusters.

17. The method of claim 13, further comprising, after step (c), maintaining the in vitro cell culture in a medium in the absence of bFGF.

18. The method of claim 13 wherein the medium comprises DMEM.

19. The method of claim 13 wherein the medium comprises F12.

20. The method of claim 13 wherein the medium comprises FGF-8.

21. The method of claim 13 wherein the medium comprises a member of the group consisting of retinoic acid, dbcAMP, BDNF, and GDNF.

22. The method of claim 21, wherein the cells are plated onto a substrate that comprises a member of the group consisting of poly L-lysine, polyornithine, and extracellular matrix.

23. The method of claim 13, wherein the concentration of the bFGF is in the range of 0.05 to 1000 ng per ml.

24. The method of claim 13, wherein heparin is present with the bFGF.

25. The method of claim 13 wherein the compound comprises at least one neurotrophin.

* * * * *

UNITED STATES PATENT AND TRADEMARK OFFICE
CERTIFICATE OF CORRECTION

PATENT NO.    : 6,897,061 B1
DATED         : May 24, 2005
INVENTOR(S)   : Tuija Helina Salin-Nordstrom It is certified that error appears in the above-identified patent and that said Letters Patent is hereby corrected as shown below:

Column 10,
Line 20, insert -- in either the 2-day or 5-day groups, indicating that no neurons were present. Therefor cell -- after the words "positive cells".

Signed and Sealed this

Sixteenth Day of August, 2005

JON W. DUDAS
*Director of the United States Patent and Trademark Office*